(12) United States Patent
Zammit

(10) Patent No.: US 6,183,493 B1
(45) Date of Patent: Feb. 6, 2001

(54) METHOD AND APPARATUS FOR THE TREATMENT OF SLEEP APNEA AND RELATED BREATHING DISORDERS

(75) Inventor: Gary Zammit, Norwalk, CT (US)

(73) Assignee: Pharmasys International, LLC, Norwalk, CT (US)

(*) Notice: Under 35 U.S.C. 154(b), the term of this patent shall be extended for 0 days.

(21) Appl. No.: 09/379,606

(22) Filed: Aug. 24, 1999

(51) Int. Cl.[7] .................................................. A61M 29/00

(52) U.S. Cl. ............................................................ 606/196

(58) Field of Search ............................. 606/196, 199, 606/204.45; 128/207.18

(56) References Cited

U.S. PATENT DOCUMENTS

| 3,568,678 | 3/1971 | Pourquier | 128/348 |
|---|---|---|---|
| 3,867,946 | 2/1975 | Huddy | 128/351 |
| 4,275,724 | 6/1981 | Behrstock | 128/207.14 |
| 4,655,213 | 4/1987 | Rapoport et al. | 128/205.25 |
| 4,821,715 | 4/1989 | Downing | 128/207.18 |
| 5,065,756 | 11/1991 | Rapoport | 128/204.18 |
| 5,094,233 | * 3/1992 | Brennan | 606/196 |
| 5,139,510 | * 8/1992 | Goldsmith, III et al. | 606/196 |
| 5,176,618 | 1/1993 | Freedman | 600/12 |
| 5,185,005 | 2/1993 | Ballantyne | 604/174 |
| 5,456,694 | 10/1995 | Marin et al. | 606/198 |
| 5,464,011 | 11/1995 | Bridge | 128/207.14 |
| 5,484,444 | 1/1996 | Braunschweiler et al. | 606/108 |
| 5,507,768 | 4/1996 | Lau et al. | 606/198 |
| 5,639,276 | 6/1997 | Weinstock et al. | 606/129 |
| 5,664,567 | 9/1997 | Linder | 128/207.18 |
| 5,791,337 | 8/1998 | Coles et al. | 128/200.26 |

OTHER PUBLICATIONS

Sanders, "Medical Thereapy for Sleep Apnea," Principles and Practice of Sleep Medicine, 2$^{nd}$ Edition, pp. 678–684.

Afzelius, et al., "Sleep Apnea Syndrome–An Alternative Treatment to Tracheostomy," The Laryngoscope, 91 (1981) pp. 285–291.

Sullivan et al., "Reversal of Obstructive Sleep Apnea by Continuous Positive Airway Pressure Applied Through the Nares," The Lancet, (1981) pp. 862–865.

Fujita et al., "Surgical Correction of Anatomic Abnormalities in Obstructive Sleep Apnea Syndrome: Uvulopalatopharyngoplasty," Otolaryngol Head Neck Surg 89, (1981) pp. 923–934.

Krieger et al., "Objective measurement of compliance with nasal CPAP treatement for obstructive sleep apnoea syndrom," The European Respiratory Journal, No. 1, (1988) pp. 436–438.

Sanders et al., "Patient Compliance with Nasal CPAP Therapy for Sleep Apnea," Chest, 90, (1986) pp. 330–333.

Nahmias et al., "Treatment of the Obstructive Sleep Apnea Syndrome Using a Nasopharyngeal Tube," Chest, 94, pp. 1142–1147.

Sanders et al., "CPAP Via Nasal Mask: A Treatment for Occlusive Sleep Apnea," Chest, 83, pp. 144–145.

(List continued on next page.)

Primary Examiner—Michael Buiz
Assistant Examiner—Kevin Truong
(74) Attorney, Agent, or Firm—Morgan & Finnegan, L.L.P.

(57) ABSTRACT

The present invention is a collapsible nasal-oropharyngeal tube and a method of its use. The collapsed tube is inserted via a patient's nostril, then expanded when properly located in the upper airway. Collapsing the tube prior to insertion, facilitates insertion, minimizes trauma to the nasal passage, and allows self insertion by the patient. The expanded tube's lumen defines an unobstructed airway, and thus maintains upper airway patency. The nasal-oropharyngeal tube can be used as a treatment of nasal-oropharyngeal obstructions, sleep apnea, and other related disorders.

15 Claims, 4 Drawing Sheets

OTHER PUBLICATIONS

Kribbs et al., "Objective Measurement of Patterns of Nasal CPAP Use by Patients with Obstructive Sleep Apnea," American Review of Respiratory Disease, vol. 147, No. 4, (1993) pp. 887–895.

Kamami, Laser $CO_2$ for Snoring Preliminary Results, ACTA Oto–Rhino–Laryngologica Belgica, vol. 44, No. 4, (1990) pp. 451–456.

* cited by examiner

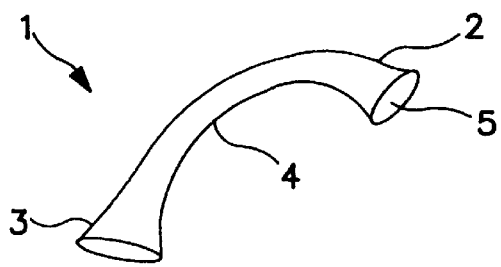
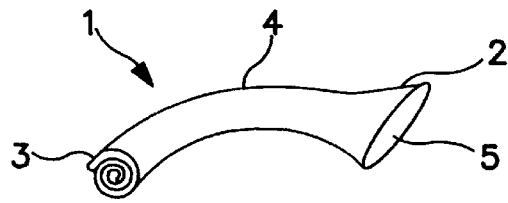
FIG. 1  FIG. 2
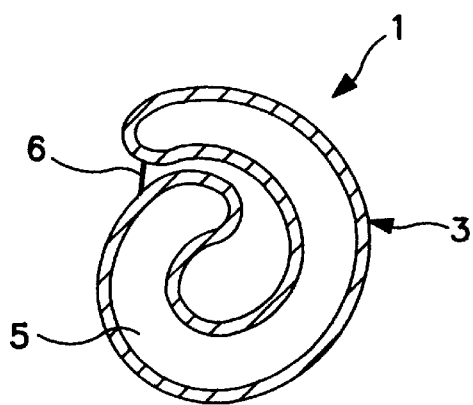
FIG. 3
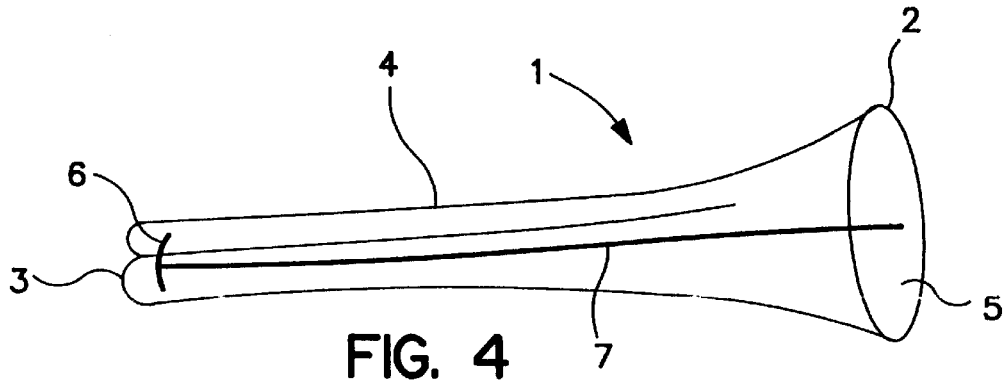
FIG. 4

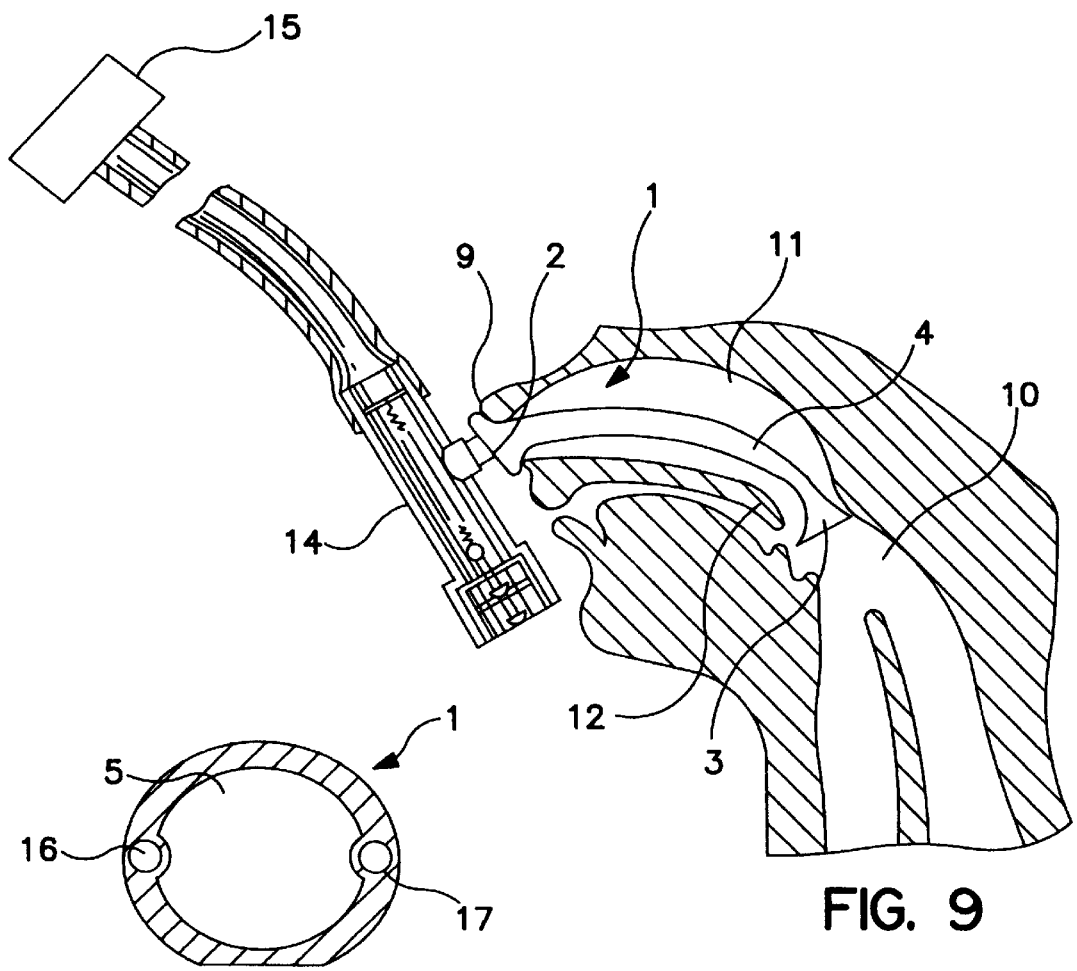
FIG. 9
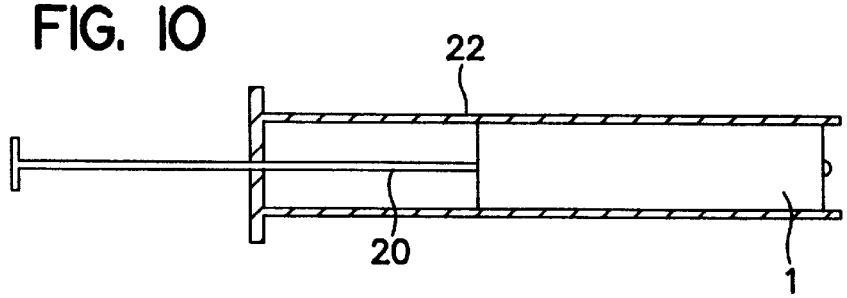
FIG. 10
FIG. 11
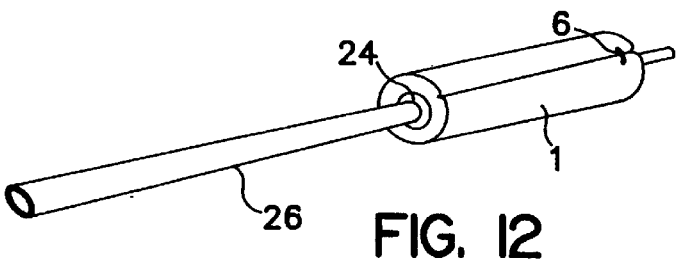
FIG. 12

METHOD AND APPARATUS FOR THE TREATMENT OF SLEEP APNEA AND RELATED BREATHING DISORDERS

BACKGROUND

1. Field of the Invention

This invention relates to a method and apparatus for treating nasal-oropharyngeal obstructions, sleep apnea, and related breathing disorders. More particularly, this invention relates to an improved method and a device for maintaining nasal-oropharyngeal airway patency.

2. Description of the Related Art

Sleep apnea is a sleep-related breathing disorder that is thought to affect between 1–10% of the adult population. Recent epidemiologic data indicate that 2% of women and 4% of men between the ages of 30 and 60 years meet the minimum diagnostic criteria for sleep apnea syndrome, representing more than 10 million individuals in the United States. It is a disorder with significant morbidity and mortality, contributing to increased risk of hypertension, cardiac arrhythmias, stroke, and cardiovascular death. Current treatments include nasal continuous positive airway pressure ("CPAP"), bi-level positive airway pressure ("BiPAP"), surgery, and other treatments. However, while CPAP and BiPAP are effective, up to 50% of patients discontinue treatment due to inconvenience and discomfort.

Sleep apnea is characterized by multiple respiratory pauses during sleep. These pauses, or apneas, are defined as the complete cessation of airflow in nasal and oral airways lasting at least 10 seconds. Partial reductions in airflow, known as hypopneas, are defined as the reduction of airflow in the nasal and oral airways lasting at least 10 seconds. Apneas and hypopneas result from the complete or partial obstruction of the upper airway, and can cause oxygen desaturation, arousal from sleep, or both. Any condition that interferes with airway patency can contribute to or result in the occurrence of such events. Therefore, the maintenance of upper airway patency is the primary goal of treatment of patients with sleep apnea. Upper airway patency can conveniently be achieved by maintaining nasal-oropharyngeal airway patency.

One common method for treating sleep apnea is the use of nasal continuous positive airway pressure ("CPAP") as disclosed in U.S. Pat. No. 5,065,756. Nasal CPAP is administered by means of a mechanical device that delivers pressurized room air to the nasal passage, or airway, through a nose mask that is worn by the patient. This device helps to maintain upper airway patency by means of a "pneumatic splint." (Sullivan et al., 1981, Lancet, 1, 882–865; Sanders, 1983, Chest, 83, 144–145). However, compliance with, and long-term acceptance of, this treatment are poor. Studies have shown that between 20% and 50% of patients fail to use nasal CPAP as prescribed (Sanders, et al., 1986, Chest, 90, 330–333; Krieger & Kurtz, 1988, Europ. Respira. J., 1, 436–438; Kribbs, et al., 1993, Am Rev. Respir. Dis., 147, 887–895).

Other treatments for sleep apnea include the use of a tongue retaining device and other oral appliances (Lowe, 1994, Principles and Practice of Sleep Medicine, Philadelphia, Suanders), and surgical procedures such as uvulopalatopharyngoplasty (UPPP) and laser-assisted uvulopalatopharyngoplasty (LAUP) (Fujita, 1981, Otolaryngo. Head Neck Surg., 89, 923–934; Kamami, 1990, Acta Otorhino-laryngol Belgica, 44, 451–456). However, the efficacy of these treatments is generally poor, with significant improvement achieved in fewer than 1/3 of the patients treated.

The failure of current therapies to provide effective and tolerable treatment for sleep apnea has led to consideration of novel devices. It has been suggested that sleep apnea can be treated with the use of a nasopharyngeal tube (Nahnias & Karetzky, 1988, Chest, 94, 1142 1147; Afzelius, et al., 1981, Laryngoscope, 91, 285–291). Nasopharyngeal tube therapy has resulted in a reduction in apneas and hypopneas, decreased stage I (light) sleep, increased rapid-eye-movement (REM) sleep, and subjective improvement in daytime sleepiness.

While the apparatuses described in the prior art, for example, U.S. Pat. No. 5,664,567 and U.S. Pat. No. 4,821,715 are nasopharyngeal tubes that can be inserted into the airways of patients with sleep apnea, these devices were designed to be inserted by a physician, not a patient. These tubes are difficult to insert and are not appropriate for nightly use at home by the patient. It is desirable to further refine the method and apparatus to provide an effective, convenient, and tolerable treatment for sleep apnea.

Therefore, a need still exists for an improved upper airway patency device having greater acceptance among patients that is effective, and that may be easily inserted by patients.

SUMMARY OF THE INVENTION

This invention relates to a method and device for treating nasal-oropharyngeal obstructions, sleep apnea, and related breathing disorders. In one embodiment of the present invention, the device comprises a collapsible nasal-oropharyngeal tube made from a resilient semi-rigid plastic, for example, a hypoallergenic plastic such as PVC or polyurethane. The device is collapsed to facilitate insertion, and is held in its collapsed state by a restraint such as, for example, a tie or clasp. The patient inserts the collapsed device into the upper airway until the device's distal end is located near the pharynx, and optionally beyond the soft palate, while the proximate end is located near the nostril opening. A lubricating anaesthetic may be applied to the device to ease insertion. Once the device is inserted, the patient releases the restraint to expand the device. The expanded tubular device maintains nasal passage patency, and the device's lumen maintains an unobstructed airway from the nostril to the oropharynx.

The device's proximate and distal ends can be flared or flanged to facilitate the device's correct positioning in the patient, to reduce airflow turbulence around the around the oropharynx, and to reduce the risk of airway collapse.

Therefore it is an object of the present invention to provide a tubular device, or nasal-oropharyngeal tube that is collapsible, and so can be inserted more easily through a patient's nasal passage either by the patient, or by medical staff.

Another object of the present invention is to provide a nasal-oropharyngeal tube that causes minimal irritation, discomfort, and ulceration during insertion and use.

Still another object of the present invention is to provide a self-administered treatment for sleep apnea that may be a highly desirable alternative to CPAP, BiPAP, surgery, or other treatments.

Another object of the present invention is to provide a nasal-oropharyngeal tube that may be used as an interface to nasal CPAP.

Yet another object of the present invention is to provide a nasal-oropharyngeal tube that is an effective, convenient, and comfortable treatment of nasal passage obstructions and sleep apnea.

In addition to treating sleep apnea, an airway patency device that is easily inserted into the upper airway has many other uses. It may be used by patients with sleep-related breathing disorders other than sleep apnea, such as snoring or upper airway resistance syndrome. It may be used by medical staff, for example, by anesthesiologists requiring an alternative to traditional nasopharyngeal tubes. It also may be used as an interface to nasal CPAP, replacing the need for nasal CPAP masks, such as the apparatus disclosed in U.S. Pat. No. 4,655,213.

Other features and advantages of the invention will be apparent from the following description of embodiments thereof and from the claims.

BRIEF DESCRIPTION OF THE DRAWINGS

FIG. 1 is a view of an embodiment of an expanded nasal-oropharyngeal tube of the present invention.

FIG. 2 is a view of the collapsed nasal-oropharyngeal tube illustrated in FIG. 1.

FIG. 3 is a distal end cross-section view of the collapsed nasal-oropharyngeal tube illustrated in FIG. 2.

FIG. 4 is a side view of the collapsed nasal-oropharyngeal tube illustrated in FIG. 2.

FIG. 9 is a cross-section view of a patient with an expanded nasal-oropharyngeal tube of the present invention inserted and used in conjunction with CPAP apparatus.

FIG. 10 is a mid-section cross-section view of an expanded nasal-oropharyngeal tube including secondary lumens.

FIGS. 11 and 12 is a view of another embodiment of the present invention.

DETAILED DESCRIPTION OF THE INVENTION

Figure 5:
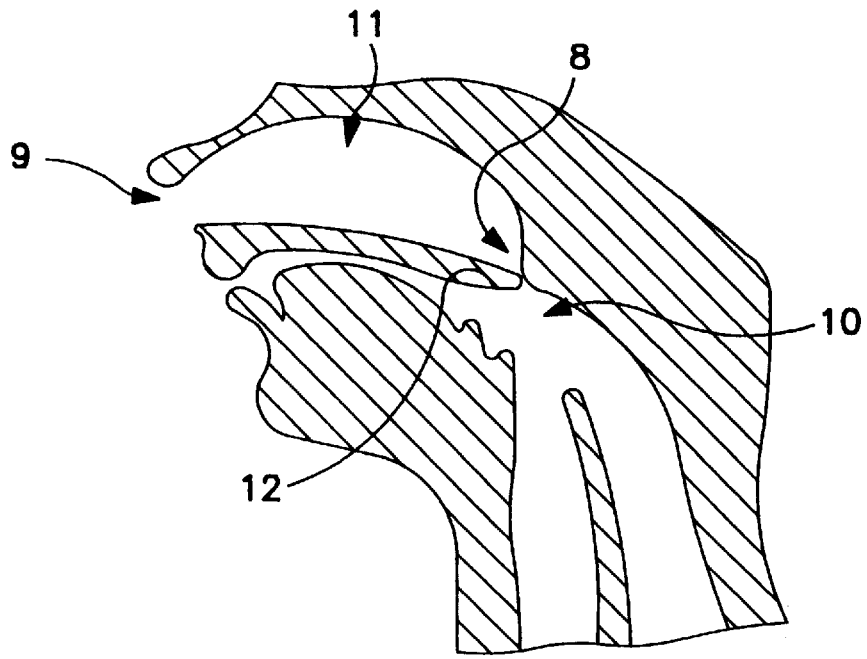
FIG. 5 is a cross-section view of a patient with a nasal-oropharyngeal obstruction.

The present invention relates to a collapsible nasal-oropharyngeal tube or device. While collapsed, the device can be inserted into a patient's nasal passage via the nostril. The device can be expanded when properly positioned in the nasal passage so as to push against the oropharynx and nasal passage walls, and thus maintain upper airway patency.

In the embodiment shown in FIG. 1, the nasal-oropharyngeal tube or device 1 comprises a semi-rigid tube made from a resilient material, the material being capable of regaining its original shape after being coiled, folded, or similarly deformed. Suitable materials include, for example, nylon, polyethylene, and polypropylene. Hypoallergenic materials such as PVC and polyurethane can be used to minimize the risk of allergic reaction in a patient.

In its expanded state shown in FIG. 1, the device 1 can have a tubular mid-section 4, a flared or flanged proximate end 2, and a flared or flanged distal end 3. The expanded device's lumen 5 defines an unobstructed airway sufficient in size to maintain the free flow of air, yet small enough to allow the device 1 to comfortably fit within a nasal passage.

To reduce the device's width compared with its width when expanded, and facilitate its insertion into the nasal passage, the device 1 can be coiled, folded, or otherwise collapsed at least at its distal end as shown in FIG. 2 and FIG. 3. FIG. 4 shows one embodiment where the device is collapsed into a narrow tapered cone-like shape, with the distal end 3 narrower than the proximate end 2. The device can be held in this collapsed state by one or more retaining mechanisms 6 such as a retaining fiber, tie or clasp, shown in FIG. 3. These retaining fibers can be connected between points around the circumference of the device 1 as shown in FIG. 3, or they can, for example, be tied around the entire circumference of the device 1. As shown in FIG. 4, the device can further comprise a retaining mechanism release. The retaining mechanism release can be a release fiber 7 connected at its distal end to the retaining mechanism. The release fiber 7 can run along the length of the device so that the fiber's proximate end extends beyond the device's proximate end 2. The patient, or user, can release the retaining mechanism by, for example, pulling the proximate end of the release fiber 7 to break the retaining tie 6. In this embodiment, the end of the release fiber 7 may be exposed at the nostril after the device 1 is inserted.

Figure 6:
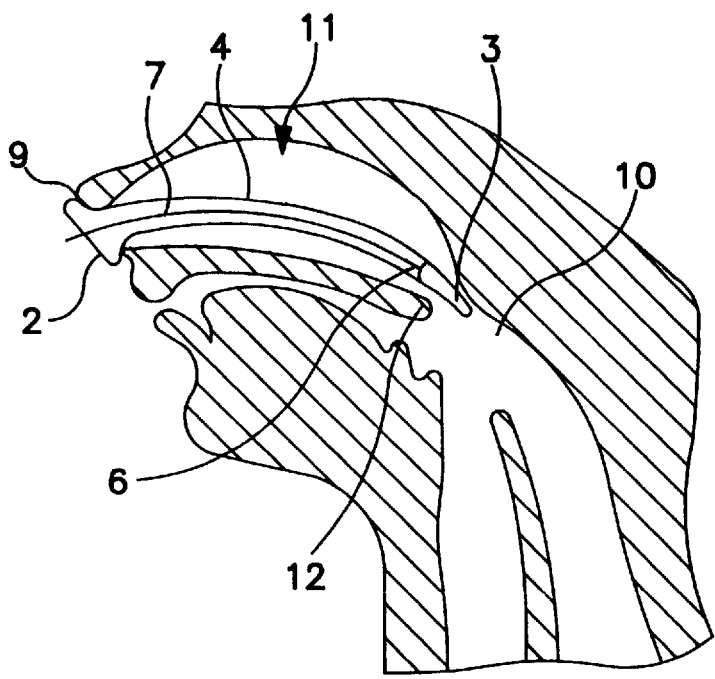
FIG. 6 is a cross-section view of a patient with a collapsed nasal-oropharyngeal tube of the present invention inserted.

FIG. 5 shows a patient suffering from a nasal-oropharyngeal obstruction 8. Also shown is a nostril opening 9, the oropharynx 10, the nasal passage 11, and the soft palate 12. In an embodiment shown in FIG. 6, a patient inserts the collapsed nasal-oropharyngeal tube via the nostril 9 and through the nasal passage 11 until the device is properly positioned. When properly positioned the proximate end flange 2 should be located at the nostril 9, and the distal end flange 3 should lie at the oropharynx 10 just beyond the soft palate 12. The device 1 is sufficiently long to extend from the nostril's 9 opening to the oropharynx 10, optionally just beyond the soft palate 12. The device may be made in several lengths and diameters to accommodate varying nostril-oropharynx distances and nasal passage widths in different patients. Typical lengths may, for example, range from 10 cm to 16 cm and mid-section diameters from 5 mm to 10 mm.

Figure 7:
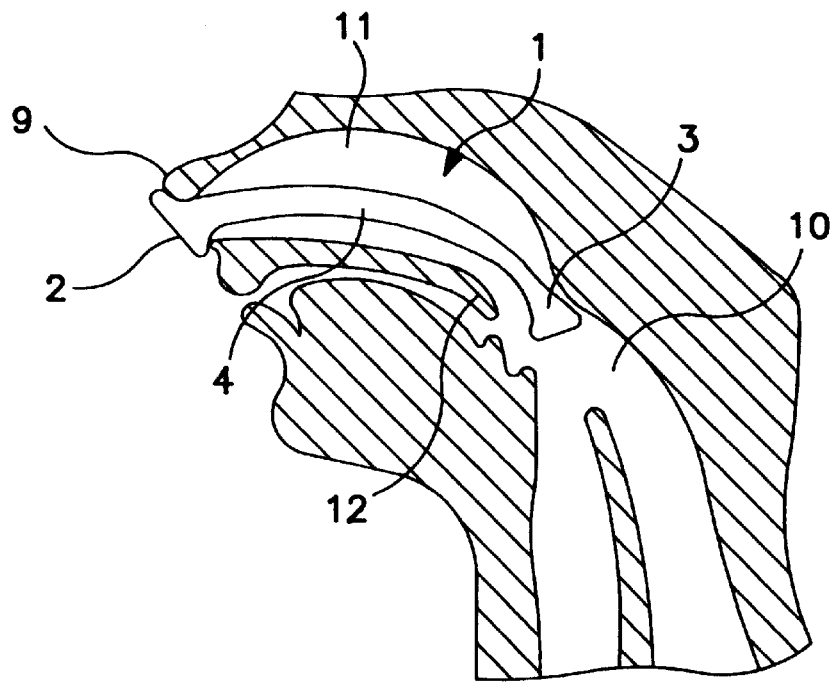
FIG. 7 is a cross-section view of a patient with a nasal-oropharyngeal tube of the present invention inserted and expanded.

With the collapsed device 1 properly positioned the release fiber 7 can be pulled, breaking the tie 6, and allowing the collapsed device 1 to expand as shown in FIG. 7. With the device expanded, the distal end flange 3 can reduce turbulent airflow at the oropharynx 10, and help maintain airway patency.

To facilitate device 1 insertion an anaesthetic, such as xylocaine in a lubricant or gel form, can be applied to the nasal passage 11 prior to or during inserting the device 1. One method of applying anaesthetic is to coat the collapsed device 1 with anaesthetic lubricant prior to insertion.

Figure 8:
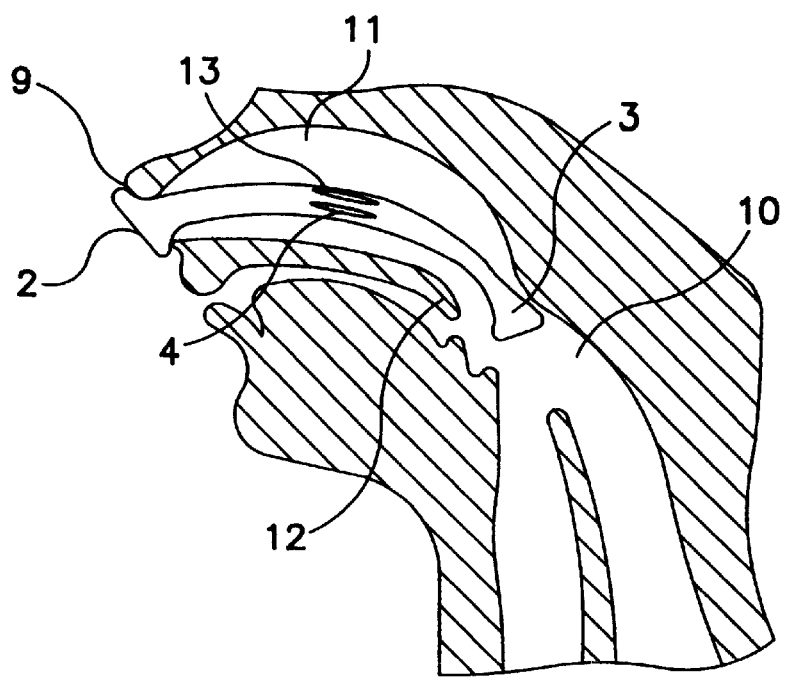
FIG. 8 is a cross-section view of a patient with a nasal-oropharyngeal tube having fenestrations inserted and expanded.

The collapsible nasal-oropharyngeal tube 1 of the present invention may advantageously incorporate other features. For example, in another embodiment of the present invention shown in FIG. 8, the device 1 can include multiple openings or fenestrations 13 in its mid-section 4. The fenestrations allow secretions from the sinus ostia and other parts of the skull, that would otherwise be trapped by the expanded device 1, to drain through the fenestrations 13 and outwards through the nasal-oropharyngeal tube 1. Thus, the fenestrations 13 can reduce the chance of infection, headaches, and other deleterious effects resulting from the buildup of undrained fluids.

In another embodiment of the present invention shown in FIG. 9, the collapsible nasal-oropharyngeal tube 1 can be used in conjunction with other airway obstruction treatments such as CPAP. For example in CPAP, a nose mask is normally connected to a breathing air compressor via a regulating valve. In the present embodiment of the invention, however, the nasal-oropharyngeal tube 1 can replace the nose mask, so that the tube 1 is connected to the compressor 15 via the regulating valve 14.

In another embodiment shown in FIG. 10, the collapsible nasal-oropharyngeal tube 1 may also advantageously incorporate secondary internal lumens 16 and 17 in addition to lumen 5. These secondary lumens 16 and 17 permit ancillary tubes (not shown) to be introduced, for example, for supplying oxygen or for suction. The ancillary lumens 16 and 17 can reduce the trauma associated with repeated insertion of ancillary tubes.

In another embodiment of the present invention, the collapsible nasal-oropharyngeal tube 1 can be deployed using an implanting device. One type of device shown in FIG. 11, for example, can comprise a flexible tube or sheath 22 insertable into the nasal-oropharyngeal airway, and a guide wire or mandrel 20 passing through the lumen of the sheath 22. The outer walls of the sheath 22 can be coated with an anaesthetic lubricant to ease insertion into the nasal passage. The distal end of the mandrel can have a rounded tip to prevent injuring the nasal passage during the implanting device's insertion. In preparation for deploying the nasal-oropharyngeal tube 1, a collapsed nasal-oropharyngeal tube 1 can be located on the mandrel, so that the mandrel passes through the nasal-oropharyngeal tube's lumen, and the sheath 22 passes over the collapsed nasal-oropharyngeal tube 1. The nasal-oropharyngeal tube can be held in its collapsed state by the surrounding walls or lumen of the sheath 22, no retaining tie or release fiber is required on the nasal-oropharyngeal tube. The prepared implanting device can be inserted into the nasal passage until the collapsible nasal-oropharyngeal tube 1 is properly positioned. To deploy the nasal-oropharyngeal tube 1, the sheath 22 can be pulled back relative to the mandrel 20 uncovering the nasal-oropharyngeal tube, and allowing the nasal-oropharyngeal tube 1 to expand. Once the nasal-oropharyngeal tube is deployed, the implanting device can be removed from the nasal-oropharyngeal airway.

An alternative implanting device, shown in FIG. 12, can comprise a mandrel having an expandable diameter. For example, the mandrel can comprise a first mandrel 26 surrounded over a portion of the first mandrel's 26 length by an inflatable bladder 24 that can be expanded by inflating with fluid, or collapsed by releasing fluid. A collapsed nasal-oropharyngeal tube 1, held in its collapsed state by, for example, a retaining tie 6, can be loaded around the collapsed inflatable bladder. When the implanting device and the nasal-oropharyngeal tube 1 are properly inserted into the nasal-oropharyngeal airway, the bladder 24 can be inflated, causing the retaining tie 6 to be released, or break, and allowing the nasal-oropharyngeal 1 tube to expand. The fluid in the bladder 24 can optionally then be released and the implanting device can be removed.

While particular embodiments of the present invention have been illustrated and described herein, the present invention is not limited to such illustrations and descriptions. It is apparent that changes and modifications may be incorporated and embodied as part of the present invention within the scope of the following claims.

What is claimed is:

1. A device comprising:
a collapsible nasal-oropharyngeal tube having a proximate end and a distal end, and having expanded and collapsed states, wherein in the expanded state the distal end of the nasal-oropharyngeal tube is flared, and wherein in the expanded state the lumen of said tube defines an unobstructed airway, and in the collapsed state at least said tube's distal end width is reduced; and
a retaining mechanism connected to said tube;
wherein said retaining mechanism is capable of holding said tube in a collapsed state, and wherein said tube, when collapsed, is insertable into a patient's nasal-oropharyngeal airway.

2. The device of claim 1, further comprising a retaining mechanism release connected to the retaining mechanism.

3. The device tube of claim 2, wherein the tube is expandable by releasing the retaining mechanism, wherein the lumen of the expanded tube defines an unobstructed airway, and wherein the expanded tube can maintain nasal-oropharyngeal patency.

4. The device of claim 2, wherein the retaining mechanism release is a release fiber connected at its distal end to the retaining mechanism, and capable of breaking the retaining mechanism if pulled.

5. The device of claim 1, wherein the tube can extend from the nostril opening to the oropharynx of a patient.

6. The device of claim 1 wherein the largest diameter of the expanded tube is located near the oropharynx.

7. The device of claim 1 wherein the tube comprises a hypoallergenic material.

8. The device of claim 1 wherein the tube comprises PVC, polyurethane, polyethylene or polypropylene.

9. The device of claim 1, further comprising an anesthetic coating.

10. The device of claim 1, further comprising a lubricant coating.

11. The device of claim 1, further comprising fenestrations in the nasal-oropharyngeal tube.

12. The device of claim 1, further comprising a continuous positive airway pressure compressor connected via a regulating valve to the proximate end of the nasal-oropharyngeal tube.

13. The device of claim 1, further comprising an implanting device, the implanting device comprising a mandrel wherein at least a portion of the length of the mandrel is expandable and collapsible,
wherein the mandrel is mounted collapsed through the lumen of the nasal-oropharyngeal tube,
wherein the nasal-oropharyngeal tube is collapsed,
wherein the expandable portion of the mandrel is located within the nasal-oropharyngeal tube's lumen, and
wherein the mandrel is capable of releasing the retaining mechanism by expanding.

14. A device comprising:
a collapsible nasal-oropharyngeal tube having expanded and collapsed states, wherein in the expanded state the lumen of said tube defines an unobstructed airway, and in the collapsed state at least said tube's distal end width is reduced, wherein the nasal-oropharyngeal tube is collapsed;
a mandrel mounted through the lumen of the nasal-oropharyngeal tube; and
a sheath having a lumen, wherein the sheath covers the nasal-oropharyngeal tube and the sheath's lumen retains the nasal oropharyngeal tube in a collapsed state;
wherein the device is insertable into a patient's nasal-oropharyngeal airway, and wherein the nasal-oropharyngeal tube can be deployed by inserting the device in a patient's nose, expanding the nasal-oropharyngeal tube by removing the sheath and uncovering the nasal-oropharyngeal tube, and removing the sheath and the mandrel.

15. A device comprising:

a collapsible nasal-oropharyngeal tube having expanded and collapsed states, wherein in the expanded state the lumen of said tube defines an unobstructed airway, and in the collapsed state at least said tube's distal end width is reduced;

a retaining mechanism connected to said tube; and a retaining mechanism release connected to the retaining mechanism;

wherein said retaining mechanism is capable of holding said tube in a collapsed state, wherein said tube, when collapsed, is insertable into a patient's nasal-oropharyngeal airway, wherein the tube is expandable by releasing the retaining mechanism, wherein the lumen of the expanded tube defines an unobstructed airway, and wherein the expanded tube can maintain nasal-oropharyngeal patency.

* * * * *